(12) United States Patent
Schultheis et al.

(10) Patent No.: US 11,984,238 B2
(45) Date of Patent: May 14, 2024

(54) OPTOELECTRICAL GUIDE/CONDUCTOR SYSTEM WITH ADAPTER SLEEVE

(71) Applicant: SCHOTT AG, Mainz (DE)

(72) Inventors: Bernd Schultheis, Schwabenheim (DE); Oliver Keiper, Hünstetten (DE); Christian Henn, Frei-Laubersheim (DE)

(73) Assignee: SCHOTT AG, Mainz (DE)

( * ) Notice: Subject to any disclaimer, the term of this patent is extended or adjusted under 35 U.S.C. 154(b) by 35 days.

(21) Appl. No.: 16/939,927

(22) Filed: Jul. 27, 2020

(65) Prior Publication Data

US 2021/0027917 A1 Jan. 28, 2021

(30) Foreign Application Priority Data

Jul. 26, 2019 (DE) ...................... 10 2019 120 324.4

(51) Int. Cl.
| | | |
|---|---|---|
| *H01B 11/22* | (2006.01) | |
| *G01B 7/26* | (2006.01) | |
| *G01N 27/02* | (2006.01) | |
| *H01B 13/00* | (2006.01) | |

(52) U.S. Cl.
CPC ............. *H01B 11/22* (2013.01); *G01B 7/26* (2013.01); *G01N 27/02* (2013.01); *H01B 13/0036* (2013.01)

(58) Field of Classification Search
None
See application file for complete search history.

(56) References Cited

U.S. PATENT DOCUMENTS

| | | | | |
|---|---|---|---|---|
| 4,418,984 A | * | 12/1983 | Wysocki | ............. C03C 25/1061 |
| | | | | 385/127 |
| 4,609,437 A | | 9/1986 | Kruishoop | |
| 5,135,295 A | | 8/1992 | Jen | |
| (Continued) | | | | |

FOREIGN PATENT DOCUMENTS

| | | |
|---|---|---|
| CA | 2841689 | 8/2010 |
| CN | 104155716 | 9/2018 |
| (Continued) | | |

OTHER PUBLICATIONS

Bullock et al.; Fiber Optic (Coaxial Cable and Assembly With Connector; International Publication Date Sep. 29, 1994 (Sep. 29, 1994); W. L. Gore & Associates, INC; (Year: 1994).*

(Continued)

*Primary Examiner* — Nasima Monsur
(74) *Attorney, Agent, or Firm* — Ruggiero McAllister & McMahon LLC (57) ABSTRACT

An optoelectrical guide/conductor system is provided that includes an optoelectrical guide/conductor arrangement and an at least regionally electrically conductive adapter sleeve. The arrangement has an optical waveguide with an outer, organic sheath layer and a conductive layer. The conductive layer is a single layer or a sequence of layers, which is directly or indirectly on the outer sheath layer. The sleeve mechanically embraces the arrangement and electrically contacts the conductive layer such that the adapter sleeve is insertable into a connection mount, arranged e.g. on a handpiece, for transmitting optical and/or electrical signals through the conductive layer.

21 Claims, 3 Drawing Sheets

(56) References Cited

U.S. PATENT DOCUMENTS

| | | | |
|---|---|---|---|
| 5,497,442 A | 3/1996 | Roos | |
| 9,242,100 B2* | 1/2016 | Walsh | A61B 5/6852 |
| 2009/0148722 A1* | 6/2009 | Louwet | C08L 65/00 |
| | | | 528/380 |
| 2009/0296018 A1 | 12/2009 | Harle | |
| 2010/0057179 A1 | 3/2010 | Storey | |
| 2010/0272398 A1 | 10/2010 | Mihajlovic | |
| 2011/0184244 A1* | 7/2011 | Kagaya | A61B 1/00117 |
| | | | 600/182 |
| 2012/0031462 A1* | 2/2012 | Luch | H01L 31/022425 |
| | | | 136/252 |
| 2014/0321822 A1* | 10/2014 | Yasuda | G02B 6/4416 |
| | | | 385/101 |
| 2015/0041177 A1* | 2/2015 | Yasuda | G02B 6/4416 |
| | | | 174/128.1 |
| 2015/0292699 A1 | 10/2015 | Woelfing | |
| 2016/0351292 A1* | 12/2016 | Toth | A61B 5/6876 |
| 2017/0052319 A1* | 2/2017 | Schultheis | G02B 6/0008 |
| 2017/0276869 A1 | 9/2017 | Setmire | |
| 2019/0090998 A1 | 3/2019 | Ertl | |

FOREIGN PATENT DOCUMENTS

| | | |
|---|---|---|
| DE | 102006029203 | 12/2007 |
| DE | 102011003199 | 7/2012 |
| DE | 102012109088 | 5/2014 |
| JP | S5576306 | 6/1980 |
| JP | H0819557 | 1/1996 |
| WO | 9422039 | 9/1994 |
| WO | 2017120400 | 7/2017 |
| WO | 2019057316 | 3/2019 |

OTHER PUBLICATIONS

Polyvinyl chloride—Wikipedia, with English translation—Jul. 22, 2020.

ASTM F2252-13, "Standard Practice for Evaluating Ink or Coating Adhesion to Flexible Packaging Materials Using Tape", 2 pages.

DIN EN ISO 10993-1, "Biological evaluation of medical devices—Part 1: Evaluation and testing within a risk management process (ISO/DIS 10993-1:2017); German and English version prEN ISO 10993-1:2017", Apr. 2017, with English translation, 109 pages.

DIN 58196-6, "Thin layers for optics Part 6: Testing the adhesive strength with an adhesive tape", Jul. 1995, with English translation, 4 pages.

DIN EN ISO 14577-4, "Metallic materials—Instrumented indentation test for hardness and materials parameters—Part 4: Test method for metallic and nonmetallic coatings", Apr. 2017, 28 pages.

\* cited by examiner

OPTOELECTRICAL GUIDE/CONDUCTOR SYSTEM WITH ADAPTER SLEEVE

CROSS REFERENCE TO RELATED APPLICATIONS

This application claims benefit under 35 USC § 119 of German Application 10 2019 120 324.4 filed Jul. 26, 2019, the entire contents of which are incorporated herein by reference.

BACKGROUND

1. Field of the Invention

The invention relates to an optoelectrical guide/conductor system comprising an organically clad and conductively coated optical waveguide, which system is insertable into a connection mount of an apparatus with handheld operation.

2. Description of Related Art

Optical waveguides serve to transmit light or energy for numerous applications. In this case, it is sometimes desirable to enable electrical signals to be transmitted in addition to the transmission of light, for example in order to control the transmission of light depending on the electrical signals. This can be made possible by a conductive layer applied on the optical waveguide or on the cladding thereof.

The German patent application DE 10 2012 109 088 A1 describes, for instance, a fiber-optic conversion module as part of a lighting device in a vehicle, wherein optical fibers having an electrically conductive coating can be used, which allow a break of optical fibers to be ascertained. A break of an optical fiber results in an interruption of an electrical circuit path, which is ascertainable by virtue of absent or decreasing current in detection means and is used for turning off excitation light sources.

The German patent application DE 10 2006 029 203 A1 relates to a light emitting device comprising a light guide. An electrically conductive connection can be present on the surface of the cladding region of the light guide, which connection winds around the cladding region or is arranged peripherally around the light guide and can thus detect possible damage or a break of the light guide at various points.

U.S. Pat. No. 5,135,295 describes piezoelectric and ultrasonic devices that use optical fibers coated with thin piezoelectric and ferroelectric lead zirconate titanate films. The PZT thin-film layers are produced chemically by means of a solgel method.

Irrespective of a conductive coating, optical waveguides are generally also used in the field of medical technology. WO 2019057316 A1 and US 2019090998 A1 relate, for example, to a method and an arrangement for cleaning a circumferentially closed canal by means of a light guide which guides a laser beam.

SUMMARY

It has been determined by the present application that it would be desirable for optical waveguides provided for fitting to an apparatus with handheld operation or a handpiece, for example, to be able to be secured modularly and exchangeably in a simple manner, a precise arrangement and, in the case of a conductive coating, electrical contacting being made possible at the same time.

The invention relates to an optoelectrical guide/conductor system comprising an optoelectrical guide/conductor arrangement and an adapter sleeve for receiving the optoelectrical guide/conductor arrangement.

The optoelectrical guide/conductor arrangement comprises an optical waveguide having an outer, organic sheath layer, and a conductive layer consisting of a single layer or a sequence of layers, said conductive layer being applied indirectly or directly on the outer sheath layer of the optical waveguide.

The adapter sleeve is embodied such that it is at least regionally electrically conductive and serves firstly to mechanically embrace the optoelectrical guide/conductor arrangement and secondly to electrically contact the conductive layer thereof, specifically in particular in such a way that the optoelectrical guide/conductor system together with the surrounding adapter sleeve is insertable into a connection mount, arranged e.g. on an apparatus with handheld operation or a handpiece, for transmitting optical and/or electrical signals.

From a geometric standpoint, the adapter sleeve preferably has an outer sleeve body enclosing an inner receiving opening. The optoelectrical guide/conductor arrangement can then accordingly extend along a sleeve axis defined by the adapter sleeve through the inner receiving opening of the adapter sleeve.

Preferably, the inner receiving opening of the adapter sleeve is shaped in a cylindrical fashion, such that preferably an optoelectrical guide/conductor arrangement having a round cross section can be received in an appropriately fitting manner therein. Furthermore, the inner receiving opening of the adapter sleeve is preferably arranged concentrically with respect to the outer sleeve body, wherein the latter can optionally likewise be embodied in a cylindrical fashion.

Preferably, the optoelectrical guide/conductor arrangement is inserted into the adapter sleeve by one (proximal) end, wherein this end can optionally terminate flush with the adapter sleeve. The optoelectrical guide/conductor arrangement preferably projects from the adapter sleeve at least by the other (distal) end. Since light is coupled into the optical waveguide typically at the proximal end, said light leaving the optical waveguide again at the distal end, the optoelectrical guide/conductor arrangement is preferably embraced in the adapter sleeve in such a way that at least the optical waveguide is accessible from both sides of the adapter sleeve.

The distal end of the optoelectrical guide/conductor arrangement, which end generally serves for coupling out light, can be embodied as substantially flat. However, provision can also be made for the distal end of the optoelectrical guide/conductor arrangement, with regard to the substantially flat geometry of said end, to be modified and/or structured and/or roughened, in particular at least partly or in sections, e.g. in a frustoconical fashion, with an angle of less than 90° with respect to the longitudinal axis of the optoelectrical guide/conductor arrangement, for example in order to provide in a modified manner a required or aligned emission of the light that is coupled in at the proximal end and is guided therein. This can be achieved e.g. by pointing, grinding and/or polishing at least one side or by means of physical or chemical etching processes.

In order to mechanically embrace the optoelectrical guide/conductor arrangement, the adapter sleeve preferably has an, in particular dedicated, fixing section. An adhesive can be introduced in said fixing section, said adhesive additionally fixing the optoelectrical guide/conductor arrangement, wherein the adhesive has in particular a thickness of between 1 and 500 micrometers, preferably between 5 and 100 micrometers, particularly preferably between 10 and 50 micrometers, in a radial direction.

If the adapter sleeve is inserted in a complementary connection mount, light can be coupled into the optical waveguide of the optoelectrical guide/conductor arrangement via the connection mount.

In order to ensure precise input coupling as centrally as possible into the optical waveguide in this case, provision can be made for the fixing section of the adapter sleeve to embrace the optoelectrical guide/conductor arrangement with a radial tolerance of less than 50 µm, preferably of less than 30 µm.

This can be made possible in particular by the fixing section of the adapter sleeve having a radial play of less than 50 µm, preferably of less than 30 µm, vis-à-vis the optoelectrical guide/conductor arrangement. Even in the case where the insulation has been stripped from one or more outer layers of the optoelectrical guide/conductor arrangement, it is possible to provide a play of less than 50 µm, preferably of less than 30 µm, vis-à-vis the respective outermost component of the optoelectrical guide/conductor arrangement.

Particularly preferably, the fixing section of the adapter sleeve embraces the optoelectrical guide/conductor arrangement in such a way that the optical waveguide of the optoelectrical guide/conductor arrangement is embraced centrally with respect to the sleeve axis with a concentricity error of less than 50 µm, preferably of less than 30 µm.

As an alternative or in addition to the fixing section described above, the adapter sleeve can have an electrically conductive contacting section, which is in particular a dedicated electrically conductive contacting section but optionally is also formed jointly with the fixing section, which contacting section electrically contacts the conductive layer of the optoelectrical guide/conductor arrangement. An electrically conductive adhesive can be introduced in said contacting section, said adhesive electrically contacting the conductive layer of the optoelectrical guide/conductor arrangement, wherein the conductive adhesive has in particular a thickness of between 1 and 500 micrometers, preferably between 25 and 250 micrometers, particularly preferably between 50 and 150 micrometers, in a radial direction.

Provision can be made for the inner receiving opening of the adapter sleeve to have a smaller cross section in the region of the fixing section than in the region of the contacting section. In this case, a transition region from the smaller cross section to the larger cross section can be arranged between the fixing section and the contacting section, wherein such a transition region can be embodied e.g. as a cone or as a ring shoulder.

In principle, the invention can be used for optoelectrical guide/conductor arrangements and adapter sleeves of any size. It is possible e.g. for the adapter sleeve to have an external diameter of less than 20 millimeters, preferably of less than 10 millimeters, particularly preferably of less than 5 millimeters, and/or for the adapter sleeve to have an internal diameter of less than 2000 micrometers, preferably of less than 1000 micrometers, particularly preferably of less than 500 micrometers.

Since the adapter sleeve is embodied such that it is electrically conductive at least regionally, it may be appropriate for the adapter sleeve to comprise or to consist of a metal, e.g. high-grade steel or nickel silver, or a conductive plastic or a conductive ceramic.

One possible application of the optoelectrical guide/conductor system presented resides in the measurement of an impedance between the adapter sleeve, which electrically contacts in particular the proximal end of the optoelectrical guide/conductor arrangement, and the conductive layer, in particular at the distal end of the optoelectrical guide/conductor arrangement, or a conductive medium which surrounds the conductive layer and in which the optoelectrical guide/conductor arrangement can be immersed by its distal end.

Particularly for this purpose, but also independently thereof, provision can be made for an impedance to be measurable between the adapter sleeve and the conductive layer of the optoelectrical guide/conductor arrangement, wherein the impedance firstly has a conductive layer portion and secondly has a contacting portion.

In this case, the conductive layer portion can be dependent on or be formed by the impedance of the conductive layer and/or the impedance of the conductive layer with respect to a medium surrounding the optoelectrical guide/conductor arrangement. The contacting portion, by contrast, can be at least dependent on or formed by the ohmic resistance of the conductive adhesive introduced in the contacting section and/or the capacitive reactance of the conductive adhesive introduced in the contacting section.

In one preferred embodiment, the contacting portion of the impedance is less than or equal to 10 times, preferably less than or equal to 5 times, particularly preferably less than or equal to 0.5 times, the conductive layer portion of the impedance.

In particular, the described impedance measurable between the adapter sleeve and the conductive layer of the optoelectrical guide/conductor arrangement is measurable at a specific evaluation frequency or over an evaluation frequency range, wherein the evaluation frequency or the evaluation frequency range is preferably in the range of 1 Hz to 10 GHz, more preferably in the range of 10 Hz to 2.4 GHz, more preferably still in the range of 100 Hz to 1 MHz, particularly preferably in the range of 1 kHz to 100 kHz, and very particularly preferably in the range of 1 kHz to 10 kHz.

Furthermore, the impedance measurable between the adapter sleeve and the conductive layer of the optoelectrical guide/conductor arrangement is preferably measurable between the outer sleeve body of the adapter sleeve and a region of the conductive layer in a, preferably end-side, section of the optoelectrical guide/conductor arrangement projecting from the adapter sleeve.

As described, the contacting portion of the impedance can be dependent at least on the ohmic resistance and/or capacitive reactance of the conductive adhesive introduced in the contacting section. Furthermore, the contacting portion can however also be dependent, inter alia, on the ohmic resistance of the adhesive introduced in the fixing section and/or the capacitive reactance of the adhesive introduced in the fixing section.

If the optoelectrical guide/conductor arrangement comprises a barrier layer, the latter can also contribute to the contacting portion of the impedance. A barrier layer can serve to inhibit indiffusion of oxygen and/or ions of acidic or alkaline solutions into the conductive layer and can be applied e.g. directly or indirectly on the conductive layer and/or comprise or be embodied as a superficial layer of the conductive layer having at least one altered material property. A barrier layer can e.g. also be embodied as a natural oxidation layer of the conductive layer (e.g. in the case of an aluminum conductive layer), and/or as a contamination film (coat of moisture, particle contamination and/or dirt) on the conductive layer. Contact resistances of relatively high values can result here, too, without a separate barrier layer having been applied.

In the case of a barrier layer, the contacting portion can furthermore be dependent on the ohmic resistance of the barrier layer in the region of the adhesive introduced in the fixing section and/or the capacitive reactance of the barrier layer in the region of the adhesive introduced in the fixing section.

Furthermore, provision can be made for the ohmic resistance of the adapter sleeve to be between 1 and 1000 milliohms, preferably between 10 and 1000 milliohms, particularly preferably between 10 and 100 milliohms. Depending on the type of contacting and design of the adapter sleeve, this can be in particular the ohmic resistance in a radial direction through the outer sleeve body.

Furthermore, provision can be made for the ohmic resistance of the conductive layer to be between 1 and 1000 ohms, preferably between 10 and 500 ohms, particularly preferably between 10 and 100 ohms. This can be, in particular, the ohmic resistance along the longitudinal extent of the optoelectrical guide/conductor arrangement.

The above electrical properties of the optoelectrical guide/conductor system can advantageously serve to promote the measurement of an impedance or a change in impedance when the optoelectrical guide/conductor arrangement is immersed in a medium.

In accordance with one embodiment, e.g. the impedance portion of the contacting of the conductive layer that is formed by capacitive reactances and ohmic resistances of the adhesive and/or of the electrically conductive adhesive and optionally of a barrier layer at a specific evaluation frequency can be a maximum of 10 times, preferably a maximum of 5 times, particularly preferably a maximum of 0.5 times, the impedance of the conductive layer and/or the impedance of the conductive layer with respect to a conductive medium surrounding the guide/conductor system.

In this case, the evaluation frequency can be in the range of 100 Hz to 1 MHz, preferably in the range of 1 kHz to 100 kHz, and particularly preferably in the range of 1 kHz to 10 kHz. Higher frequencies may be less suitable in some cases since, if appropriate, RF interference may already occur in the RF range. On the other hand, in some cases, excessively high impedances may result from excessively low frequencies at the capacitive transitions.

The optoelectrical guide/conductor arrangement (received in the adapter sleeve) will be discussed in even greater detail below.

As explained further above, the optoelectrical guide/conductor arrangement comprises an optical waveguide having an outer, organic sheath layer. A functional layer system can be arranged on the outer sheath layer, which functional layer system can comprise a base layer region, wherein the electrically conducting conductive layer can be applied on the base layer region. The base layer region can consist of a single layer or of a sequence of layers. The electrically conducting conductive layer can likewise consist of a single layer or a layer sequence.

The optical waveguide, on the outer sheath layer of which the conductive layer or optionally a functional layer system is situated, can be embodied in various ways, as is known to the person skilled in the art. The optical waveguide typically comprises at least one optically guiding core, preferably composed of glass, in particular quartz glass, into which electromagnetic radiation, for example that from a laser, can be coupled. The core can be surrounded directly by a cladding situated between the core and the outer sheath layer. Such a cladding can likewise be composed of quartz glass. In this case, the inner core has a greater refractive index than the cladding. The core preferably has a diameter of 10 to 600 μm, and the cladding typically has a diameter corresponding to 1.1 to 1.5 times the core diameter; the wall thickness of the sheath layer is preferably in the range of 1 to 100 μm. Provision can also be made for the inner core to be surrounded directly by the outer sheath layer. In this case, the refractive index of the core is greater than that of the sheath layer.

In one embodiment, provision can also be made for the functional layer system to be situated directly on the optically guiding core. In this embodiment, the optical waveguide accordingly does not comprise an outer sheath layer. In other words, e.g. a pure quartz glass fiber can be provided, wherein the functional layers are applied directly thereon and can be terminated in particular by a last polymeric layer.

The organic sheath layer surrounding the core, which sheath layer can also be embodied as a size, preferably comprises polyamide (PA), polyimide (PI) or polymethyl methacrylate (PMMA) or wax, waxlike constituents or alkylsilane or is produced from at least one of these materials.

As explained, a functional layer system situated on the sheath layer can comprise a base layer region situated below the conductive layer. The base layer region can be embodied as a layer applied on the outer sheath layer and comprising an oxide, in particular $SiO_2$, $TiO_2$, $Al_2O_3$, $SnO_2$, $HfO_2$, or a boride, carbide, nitride, oxynitride, carbonitride or a metal, in particular Si, Ti, Mo or Cr, or as a sequence of such layers applied on the outer sheath layer. In other words, the outer sheath layer can be coated with a single layer or with a plurality of layers forming a base layer region. Such a layer or layer sequence can be producible or produced for instance by means of a coating method, as explained in greater detail further below. A base layer region can be embodied in particular as an inorganic adhesion promoter layer based on oxides, such as $SiO_2$, $TiO_2$, $Al_2O_3$, $SnO_2$, $HfO_2$, etc., borides, carbides, nitrides, oxynitrides, carbonitrides, or metals, such as e.g. Si, Ti, Mo or Cr, as a single layer or as a layer sequence composed of these substances. Preferred layer systems comprise $TiO_2$. In other words, a base layer region preferably contains $TiO_2$ and comprises in particular a plurality of layers, wherein at least one of these layers contains $TiO_2$. These coatings can be applied inter alia by means of a sputtering process from a so-called sputtering target, wherein these materials can be present as metallic targets or as partly ceramic targets. The purity of the targets is typically specified at 99% or more. Lower purifies are also possible, however. Higher layer thicknesses may then be required in this case.

In accordance with another embodiment, a base layer region can comprise a superficial layer of the outer sheath layer having at least one altered surface property, in particular an increased surface energy and/or an increased number of oxygen radicals. Such a superficial partial layer of the sheath layer can be producible or produced for example by chemical or physical processes for altering the surface properties of the sheath layer, in particular plasma treatment (e.g. low pressure plasma or atmospheric plasma), UV treatment, arc discharge (corona), and/or by chemical treatment, e.g. by means of alkaline cleaning agents in an ultrasonic bath, or a combination of such methods, as described in greater detail further below. In other words, a base layer region or a bottommost layer of the base layer region can be formed by a radial part of the outer sheath layer comprising the outer surface. A base layer region can thus consist e.g. of a single layer, wherein said single layer is formed by means of chemical or physical processes on the basis of the outer sheath layer of the optical waveguide with regard to the surface properties. However, a base layer region can also consist of a sequence of layers, wherein e.g. the bottommost layer of a base layer region is formed by chemical or physical processes on the basis of the outer sheath layer of the optical waveguide with regard to the surface properties and further layers are applied on said bottommost layer.

Accordingly, provision can also be made for a base layer region to consist of a plurality of layers, wherein a bottommost layer is embodied as such a superficial layer of the outer sheath layer and at least one further layer of the base layer region that is situated thereabove is embodied as a layer applied on the outer sheath layer. Such a multilayered base layer region can be producible or produced e.g. by firstly the sheath layer being treated at least in sections for example by means of plasma treatment, UV treatment, arc discharge and/or chemical treatment and then the sheath layer being coated by means of a coating method. By means of the treatment, in particular, firstly the surface energy is increased; secondly, preferably free oxygen radicals are produced, which ensure a good adhesion of subsequent coatings. The treatments are preferably effected over the whole area on the fiber surface, i.e. the surface of the optical waveguide with sheath layer. Further layers can be applied on the layer applied by means of coating methods.

A base layer region preferably has a thickness of between 5 nm and 3000 nm, more preferably between 5 nm and 1000 nm, particularly preferably between 10 nm and 100 nm. Furthermore, the individual layers of a base layer region can have in each case a thickness of between 5 nm and 1000 nm, preferably between 10 nm and 100 nm. By way of example, an at least two-layered base layer region can be provided, wherein the lower layer is embodied as a superficial layer of the outer sheath layer and a layer having a thickness of between 5 nm and 1000 nm, preferably between 10 nm and 100 nm, is applied thereabove. The layer thickness can be determined depending on the coefficient of thermal expansion of the optical waveguide to be coated or of the outer polymer layer thereof in comparison with the coefficient of thermal expansion of the conductive layer.

A base layer region can be embodied in particular as an adhesion promoter layer. Accordingly, it can be provided that between the base layer region and the conductive layer applied thereon there is an adhesion that is greater than an adhesion that would exist between the outer sheath layer and an identical conductive layer applied thereon. A good adhesion results e.g. if a so-called tape test (printing ink adhesion) on the basis of ASTM F 2252/Sun Chemical-Hartmann PV 01 can be satisfied. This involves applying an adhesive strip to the coated fibers and pulling it off uniformly at a defined angle. If there is no coating on the adhesive strip after the latter has been pulled off and if no delaminations are manifested at the coating, then the test is deemed to have been passed. The adhesion can also be checked by means of an adhesion test according to DIN 58196-6 (1995 July). In other words, there may be an increased adhesion between the conductive layer, in particular the bottommost layer of the conductive layer, and the topmost layer—situated therebelow—of a base layer region, which topmost layer can be embodied as a superficial layer of the outer sheath layer having an increased surface energy and/or an increased number of oxygen radicals or as a layer applied on the sheath layer by coating. It is also possible for a base layer region to consist of a plurality of layers, wherein at least one or each layer applied above the bottommost layer has a higher adhesion on the layer situated therebelow than it would have on the layer situated below the layer situated therebelow.

Furthermore, a base layer region can be embodied as a barrier layer. Accordingly, provision can be made for a base layer region, in particular at least one of the layers of the base layer region applied on the outer sheath layer by coating, to inhibit or block indiffusion of polymer constituents, for example acids, and/or oxygen, and in particular ions of acidic or alkaline solutions, into the conductive layer. The base layer region can accordingly delay or prevent a permeation of e.g. acids, oxygen or else other constituents of the air into the lower surface of the conductive layer. Particularly during the processing of medical products, alkaline cleaning agents or disinfectors can be used (e.g. NEODISHER having a pH of approximately 11). Furthermore, the rinsing agent sodium hypochlorite (NaClO), a bleaching agent or a disinfectant can be used.

A base layer region preferably has a coefficient of thermal expansion that is between the coefficient of thermal expansion of the sheath layer and the coefficient of thermal expansion of the conductive layer. Given a predefined coefficient of thermal expansion (CTE) of the sheath layer that is e.g. in the range of $>15*E-6$ 1/K, the properties of the base layers can be chosen depending on the conductive layer used. If e.g. a molybdenum coating is used as the conductive layer, which coating typically has a CTE of $5-6*E-6$ 1/K, a base layer region having a higher CTE can be chosen. As an example, a $TiO_2$ coating having a CTE of $7-8*E-6$ 1/K may then be appropriate. Preferably, provision can be made for the coefficient of thermal expansion of the sheath layer to be greater than the coefficient of thermal expansion of the base layer region. Furthermore, provision can be made for the coefficient of thermal expansion of a base layer region to be greater than or equal to the coefficient of thermal expansion of the conductive layer. In the case of a multilayered base layer region, this holds true at least for one of its layers. Moreover, provision can be made for a base layer region to comprise a sequence of layers, each having a coefficient of thermal expansion, which ascend or descend according to the sequence of the layers. A gradient of the coefficient of thermal expansion (CTE) can also be attained by quasi-continuous variation of the composition. The choice of the materials of a base layer region can be determined depending on the coefficient of thermal expansion of the optical waveguide to be coated or of the outer polymer layer thereof in comparison with the coefficient of thermal expansion of the conductive layer.

A conductive layer applied on the base layer region preferably comprises a layer comprising titanium, silicon (optionally doped with n- or p-conducting dopants in order to increase the intrinsic conductivity), aluminum, gold, silver, molybdenum, tungsten or zirconium, in particular an alloy of one of these substances with Ni, Zn, Y, Sn, Ge, or a sequence of such layers. Ti and Mo have been found to be particularly preferred. A layer comprising or composed of molybdenum is accordingly particularly preferred, for example. In other words, the conductive layer can consist of a single layer or of a layer sequence, wherein at least one layer is composed of titanium, (doped) silicon, aluminum, gold, silver, molybdenum, tungsten, zirconium or composed of alloys of at least one of the conductive substances mentioned, Ni and alloys thereof, Zn, Y, Sn, Ge. Such a layer or layer sequence can be producible or produced for example by means of a coating method, as explained in greater detail further below.

A conductive layer applied on the base layer region can furthermore also comprise or consist of Ag, Cu, Cr, Ni, ITO, but requirements in respect of biocompatibility and cytotoxicity (ISO 10993-5:2009) may need to be taken into consideration in the medical field.

The conductive layer preferably has a thickness of between 5 nm and 6000 nm, more preferably between 5 nm and 2000 nm, particularly preferably between 10 nm and 200 nm. Furthermore, at least one of the layers or each of the layers of the conductive layer can have a thickness of between 5 nm and 2000 nm, preferably between 10 nm and 200 nm. The layer thickness can be determined depending on the electrical resistance or sheet resistance to be achieved, wherein the sheet resistance within specific layer thickness ranges is inversely proportional to the layer thickness of the conductive layer. A layer thickness of at least 5 nm has the advantage that the risk of island formation (only regional coating) is avoided and a closed layer therefore arises. In the case of island formation, no uniform conductivity results owing to the insulating regions around the conductive "islands". If appropriate, however, layer thicknesses of at least 3 nm can also be sufficient.

The conductive layer preferably has a sheet resistance of between 0.01 and 1000, preferably between 0.01 and 100, particularly preferably between 0.01 and 50 ohms/sqr (wherein the unit ohm/sqr corresponds to the unit ohm). The sheet resistance is understood to mean the electrical resistivity divided by the layer thickness. The following hold true for the electrical resistivity, for example, Ti: 8E-5 ohm cm, Si: 2 ohm cm, Au: 6E-8 ohm cm, Ag: 1E-5 ohm cm, Mo: 4.9 E-5 ohm cm. A thin 200 nm Ti coating exhibits a sheet resistance of 3.9 ohms/sqr. This results in a resistivity of 7.8*E-5 ohm*cm.

As already described further above, a barrier layer (passivation layer) applied indirectly or directly on the conductive layer can furthermore be provided, wherein said barrier layer can consist of a single layer or a sequence of layers. The barrier layer is preferably configured to inhibit or block indiffusion of oxygen and/or acids/bases, in particular ions of acidic or alkaline solutions, into the conductive layer. Particularly during the processing of medical products, alkaline cleaning agents are sometimes used (e.g. NEODISHER having a pH of approximately 11). The rinsing agent sodium hypochlorite (NaClO), a bleaching agent or a disinfectant can also be used. The barrier layer can accordingly delay or prevent a permeation of e.g. acids, oxygen or other constituents of the air into the upper surface of the conductive layer. Furthermore, the barrier coating can ensure that mechanical attacks on the conductive layer or the fiber can be reduced and it thus forms a mechanical protective film. In combination with a corresponding base layer region, the conductive layer can thus be protected against undesired diffusion on both sides.

Preferably, the barrier layer or at least one of the layers of the barrier layer has a hardness of at least 800 HV, preferably at least 1200 HV, particularly preferably at least 2000 HV, in accordance with the test standard DIN EN ISO 14577-4:2007-8. The barrier layer can thus also be embodied as a mechanical protective layer for the conductive layer, in particular for a metallic layer, and/or as protection for the optical waveguide or the sheath layer (buffer material). In particular, hard materials composed of e.g. carbides or nitrides protect owing to their increased hardness, such as e.g. AlN: HV up to approximately 2000, Si3N4: HV up to approximately 2500.

The barrier layer preferably comprises a layer applied on the conductive layer and comprising a nitride, in particular $Si_3N_4$, BN, AlN, TiN, AlSiN, SiON, SiAlON, or an alloy of one of these substances, or comprising an oxide, in particular oxides of Si, Al, Ti, Zr, Zn, Sn, Ta, Nb, Y, or a ternary system composed of at least one of these substances, or comprising a carbide, boride, oxynitride, carbonitride, or a sequence of such layers applied on the conductive layer. Layers comprising $TiO_2$, TiN, $Si_3N_4$ or $SiO_2$ are found to be particularly suitable. On account of the CTE relationships mentioned above, barrier coatings having a CTE comparable to that of the conductive layer should preferably be used. In other words, the coefficient of thermal expansion of the barrier layer can correspond to 0.5 times to 2 times, preferably 0.75 times to 1.25 times, the coefficient of thermal expansion of the conductive layer. Furthermore, the barrier layer can also consist of a single layer or of a layer sequence. Preferably, at least one layer of the barrier layer is composed of nitride, e.g. $Si_3N_4$, BN, AlN, TiN, AlSiN, or an alloy composed of one of the nitrides mentioned. Such a layer is suitable in particular for inhibiting the diffusion of atmospheric oxygen and additionally has the advantage that it is comparatively hard. Preferably moreover at least one layer, in particular a further layer, is composed of oxide, in particular oxides of Si, Al, Ti, Zr, Zn, Sn, Ta, Nb, or a ternary system composed of at least one of these substances. Such a layer forms a good barrier in particular vis-à-vis acids. For one of the layers, preferably a further layer, carbides, borides, oxynitrides, carbonitrides can be used. Furthermore, for the barrier layer and/or one of the layers of the barrier layer it is also possible, in principle, to use the materials which can also be used for the base layer region, wherein these materials depend in particular on the chemical and/or atmospheric requirements made of such an optoelectrical guide/conductor arrangement/fiber and/or components comprising such an optoelectrical guide/conductor arrangement/fiber. A layer or layer sequence can be producible or produced for example by means of a coating method, as explained in greater detail further below.

A barrier layer, in particular as described above, can accordingly comprise a layer applied on the conductive layer as a coating. However, alternatively or additionally, provision can also be made for a barrier layer, in particular as described above, to comprise or be embodied as a superficial layer of the conductive layer having at least one altered material property. By way of example, a barrier layer can also be embodied as an, in particular natural, oxidation layer of the conductive layer (e.g. in the case of an aluminum conductive layer) and/or as a contamination film (coat of moisture, particle contamination and/or dirt) on the conductive layer.

A base layer region, the conductive layer and/or a barrier layer optionally present extend(s) at least partly or in sections in the axial direction of the optical waveguide. A base layer region can have an amorphous structure, particularly if the base layer region is embodied as a superficial partial layer of the sheath layer. A base layer region can also have a crystalline or polycrystalline structure, particularly if the base layer region comprises a layer applied by coating. The conductive layer and/or a barrier layer optionally present can likewise have a crystalline or polycrystalline or, if appropriate, amorphous structure. Amorphous layers are preferred for base layer region and barrier layer in order to ensure a particularly good diffusion barrier. SiO2, Si3N4, $Al_2O_3$, AlSiOx or BN may be mentioned as typical examples of amorphous diffusion barriers; anatase or rutile TiO2, $\gamma$-$Al_2O_3$ or crystalline AlN may be mentioned as typical examples of crystalline barrier coatings. In particular, however, mixed phases of amorphous and crystalline may also be mentioned.

The optoelectrical guide/conductor arrangement can, at least partly or in sections, also have a jacket, that is to say be surrounded by a last outer sheath, wherein this last outer sheath can be embodied in a fixedly or loosely enclosing fashion. Provision can be made for a distal section of the optoelectrical guide/conductor arrangement to be stripped of insulation or to remain. The jacket can accordingly extend predominantly along the optoelectrical guide/conductor arrangement, although a part of the optoelectrical guide/conductor arrangement, in particular one end of the arrangement, has no jacket.

The invention furthermore relates to a device for detecting the immersion of an optoelectrical guide/conductor arrangement in a conductive medium, in particular within an animal or human body, wherein the device comprises an optoelectrical guide/conductor system and also an evaluation unit.

The optoelectrical guide/conductor system is embodied in particular in accordance with the explanations above. It comprises at least: an optoelectrical guide/conductor arrangement comprising an optical waveguide having an outer, organic sheath layer, and a conductive layer applied directly or indirectly on the outer sheath layer of the optical waveguide, and furthermore: an at least regionally electrically conductive adapter sleeve, which mechanically embraces the optoelectrical guide/conductor arrangement and electrically contacts the conductive layer thereof in such a way that the optoelectrical guide/conductor arrangement is immersible in the conductive medium. The evaluation unit is electrically connectable or connected to the at least regionally electrically conductive adapter sleeve firstly and an, in particular distal, end of the optoelectrical guide/conductor arrangement and/or the conductive medium and is configured to determine an impedance or change in impedance between the adapter sleeve and the end of the optoelectrical guide/conductor arrangement and/or the medium if the optoelectrical guide/conductor arrangement has been or is immersed in the conductive medium. In this way, immersion of the optoelectrical guide/conductor arrangement in the medium can be detected and/or an immersion depth of the optoelectrical guide/conductor arrangement in the medium can be determined.

Furthermore, the device for detecting immersion can be embodied in such a way that if immersion of the optoelectrical guide/conductor arrangement in the medium is detected and/or depending on the immersion depth, the coupling of light into the optical waveguide is controlled. By way of example, the coupling in of light can be activated as soon as the optoelectrical guide/conductor arrangement is immersed or is immersed to a sufficient extent in the medium. For this purpose, the device can optionally comprise an apparatus or a handpiece having a connection mount for inserting the adapter sleeve and also a light source for coupling light into the optical waveguide.

The invention furthermore relates to a method for producing an optoelectrical guide/conductor system, in particular as described above.

In this case, an at least regionally electrically conductive adapter sleeve is provided or produced. Furthermore, an optoelectrical guide/conductor arrangement is provided or produced in such a way that the optoelectrical guide/conductor arrangement at least comprises: an optical waveguide having an outer, organic sheath layer, and a conductive layer applied directly or indirectly on the outer sheath layer of the optical waveguide and consisting of a single layer or a sequence of layers. The optoelectrical guide/conductor arrangement is then inserted into the adapter sleeve in such a way that the adapter sleeve mechanically embraces the optoelectrical guide/conductor arrangement and electrically contacts the conductive layer thereof.

Preferably, the adapter sleeve provided or produced comprises a fixing section in order to mechanically embrace the optoelectrical guide/conductor arrangement, and an adhesive is introduced into the fixing section in order to additionally fix the optoelectrical guide/conductor arrangement.

Moreover, the adapter sleeve provided or produced preferably comprises an electrically conductive contacting section in order to electrically contact the conductive layer of the optoelectrical guide/conductor arrangement, and an electrically conductive adhesive is introduced into the contacting section in order to electrically contact the conductive layer of the optoelectrical guide/conductor arrangement.

The production of the optoelectrical guide/conductor arrangement itself will be discussed in even greater detail below.

Production of an optoelectrical guide/conductor arrangement can be provided, wherein an optical waveguide having an outer sheath layer is provided and the sheath layer of the optical waveguide is coated with a functional layer system. Coating with the functional layer system comprises firstly producing a base layer region consisting of a single layer or a sequence of layers and then applying (on the base layer region) an electrically conducting conductive layer consisting of a single layer or a sequence of layers.

Producing the base layer region can firstly comprise pretreating the sheath layer of the optical waveguide in order to produce a superficial layer having at least one altered surface property, in particular an increased surface energy and/or an increased number of oxygen radicals, and/or to remove residues. Producing the base layer region can secondly comprise applying (on the outer sheath layer) a layer or a sequence of layers, wherein in particular cathode sputtering, radio-frequency sputtering, reactive sputtering and/or magnetron sputtering are/is used. Besides cathode sputtering, other coating methods, in particular vacuum methods (e.g. physical vapor deposition, chemical vapor deposition (CVD, e.g. PECVD, in particular PICVD)), can also be used. Methods from the liquid phase, such as e.g. dip coating or spray coatings, are furthermore possible as further coating methods for applying one or more layers of the base layer region. Further functions such as reducing the coefficient of friction can be concomitantly functionalized in this case.

Pretreating the sheath layer in order to form the base layer region or e.g. the bottommost layer of the base layer region can be effected by means of chemical or physical processes for altering the surface properties of the sheath layer. Pretreating the sheath layer, i.e. the surface to be coated, enables good layer adhesion. In particular, by means of a plasma pretreatment (low pressure plasma or atmospheric plasma), an arc discharge (corona) and/or a chemical pretreatment, e.g. by means of alkaline cleaning agents in an ultrasonic bath, high surface energies can be generated at least temporarily, such that the adhesion can be significantly improved as a result. By means of plasmas, moreover, greases, oils or similar residues can be removed and oxygen radicals can additionally be activated. However, pretreatment methods can also be combined.

It can also be provided that firstly a lower layer of the base layer region is formed by the sheath layer of the optical waveguide being pretreated as described above, and then at least one further layer of the base layer region is applied to said lower layer, wherein in particular the abovementioned sputtering methods (or other coating methods) are used. In particular, the method step makes it possible to produce a base layer region as described in association with the optoelectrical guide/conductor arrangement.

Applying the electrically conducting conductive layer on the base layer region is likewise preferably effected by means of cathode sputtering, radio-frequency sputtering, reactive sputtering and/or magnetron sputtering. Besides cathode sputtering, once again other coating methods, in particular vacuum methods (e.g. physical vapor deposition, chemical vapor deposition (CVD, e.g. PECVD, in particular PICVD)), can also be used. The method step makes it possible in particular to apply to the base layer region a conductive layer as described in association with the optoelectrical guide/conductor arrangement.

Coating the sheath layer with a functional layer system can furthermore comprise applying a barrier layer (passivation layer) to the conductive layer, wherein the barrier layer can be applied as a single layer or as a sequence of layers and for this purpose it is possible to use in each case in particular once again cathode sputtering, radio-frequency sputtering, reactive sputtering and/or magnetron sputtering (or other coating methods, such as e.g. the abovementioned vacuum methods or the abovementioned methods from the liquid phase, such as e.g. dip coating or spray coatings). The barrier layer can also serve for reducing the coefficient of friction. The method step makes it possible in particular to apply a barrier layer on the conductive layer as described in association with the optoelectrical guide/conductor arrangement.

The abovementioned coating methods, in particular cathode sputtering methods, by which layers of the base layer region, of the conductive layer and/or of the barrier layer can be applied are preferably effected at temperatures of less than 50° C. This relatively low temperature has the advantage, in particular, that optical waveguides can be coated with an outer polymer layer.

Preferably, producing and/or applying at least two layers are/is effected in a vacuum and without vacuum breach. Accordingly, for example, firstly the base layer region can be produced in a vacuum and then the conductive layer can be applied in the same vacuum. Furthermore, a barrier layer can then also be applied in the same vacuum.

Furthermore, a medical device can be provided, in particular an endoscope, in particular for dental treatment, comprising an optoelectrical guide/conductor system as described further above. Such a medical device can be embodied e.g. as a medical fiber component with an optoelectrical guide/conductor system comprising an optical waveguide, for instance a quartz fiber, wherein the optical waveguide is coated with a conductive layer and/or a functional layer system. Such a device can be configured for example for endoscopic applications or applications in dentistry (dental treatment).

Furthermore, an industrial device can be provided, in particular a device for filling level monitoring, in particular for containers or bioreactors, comprising an optoelectrical guide/conductor system as described above. Such an industrial device can be provided for example for industrial applications, e.g. for filling level sensors in containers, bioreactors or safety monitoring systems. Filling level monitoring is made possible, in particular, in which a change in impedance, depending on whether or not the fiber is immersed in a medium, is detectable and evaluatable. A penetration depth measurement is made possible, moreover, in which a change in impedance, depending on the extent to which the fiber is immersed in a surrounding medium, is detectable and evaluatable.

Finally, provision can be made of a use of an optoelectrical guide/conductor system for industrial applications, in particular applications for filling level monitoring or safety monitoring systems, or else a use of an optoelectrical guide/conductor system for measuring a penetration depth of the optoelectrical guide/conductor arrangement into a medium by measuring an impedance of the conductive layer in the surrounding medium.

DESCRIPTION OF THE DRAWINGS

Exemplary embodiments of the invention are described below with reference to the figures, in which.

DETAILED DESCRIPTION

Figure 1:
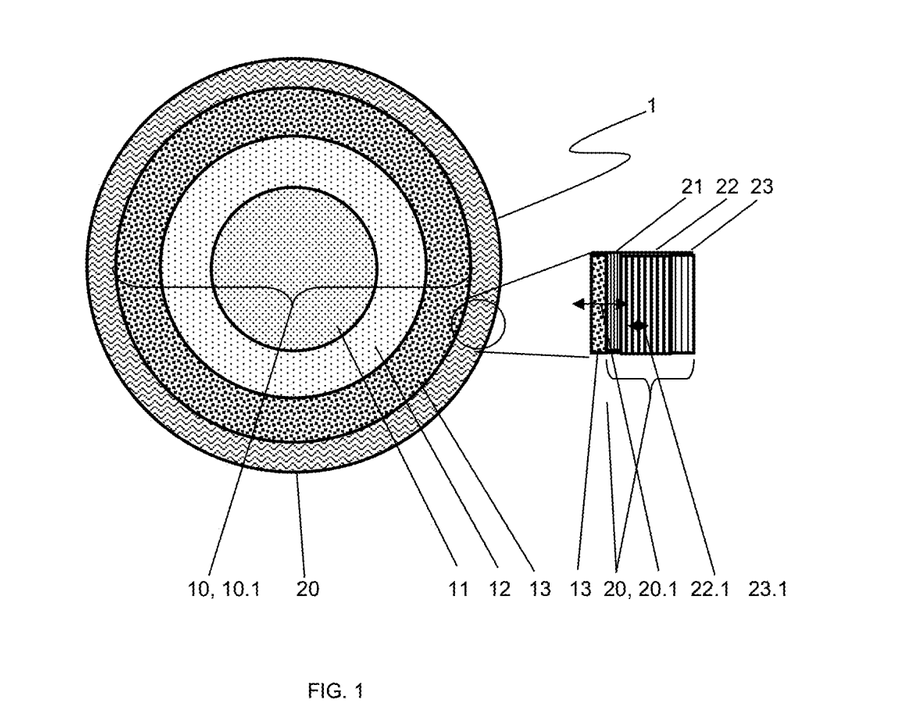
FIG. 1 shows a cross section through an optoelectrical guide/conductor arrangement (1) having an optically guiding core (11), a cladding (12), a sheath layer (13) and a functional layer system (20)

FIG. 1 shows an optoelectrical guide/conductor arrangement 1 having an optical waveguide 10 with the diameter 10.1 thereof. The optical waveguide 10 has a core 11 composed of quartz glass and a cladding 12, here likewise composed of quartz glass. The refractive index n1 of the core 11 is greater than the refractive index n2 of the cladding 12. In addition and in particular as mechanical protection, a sheath layer 13 (buffer) embodied as a polymer layer/polymer sheath is provided. The sheath layer 13, as usual for optical waveguides of this type, comprises polyimide, PMMA or polyamide, or consists of at least one of these materials.

The optoelectrical guide/conductor arrangement 1 has on the sheath layer 13 a functional layer system 20, which in this example consists of a base layer region 21 embodied as an adhesion promoter layer directly on the sheath layer 13, a conductive layer 22 and an outer barrier layer (passivation layer) 23. The functional layer system 20 on the outer sheath layer 13 is producible by means of cathode sputtering or some other vacuum method (e.g. vapor deposition). In this case, the functional layer system 20 has a layer thickness 20.1.

Figure 2:
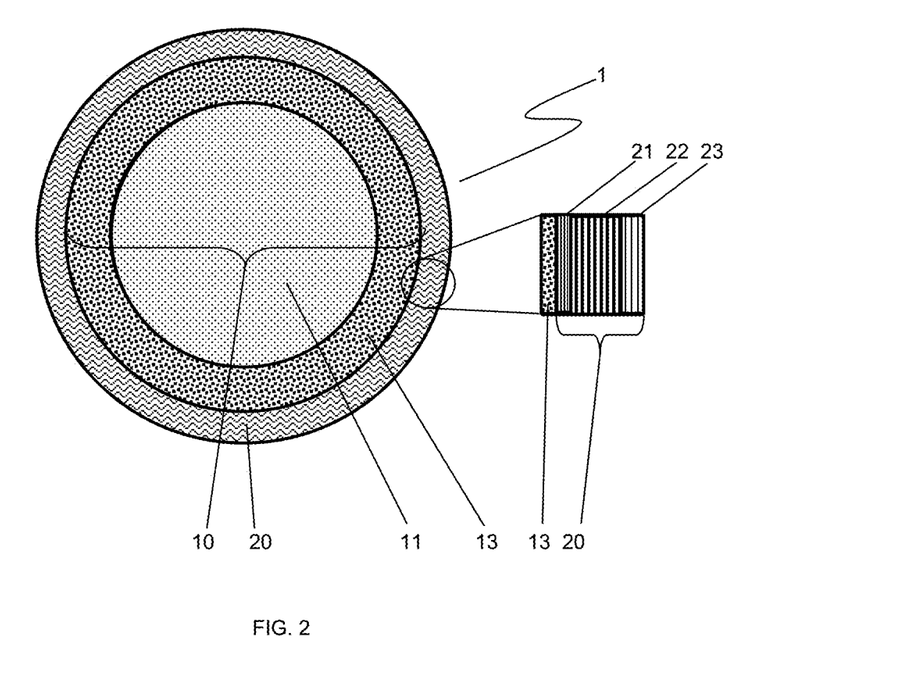
FIG. 2 shows a cross section through an optoelectrical guide/conductor arrangement (1) having an optically guiding core (11), a sheath layer (13) and a functional layer system (20)

FIG. 2 shows an optoelectrical guide/conductor arrangement 1 having an optical waveguide 10, wherein in this case the optical waveguide 10 has a core 11 and a sheath layer 13 directly surrounding the core 11. In this case, the refractive index n1 of the core 11 is slightly greater than the refractive index n2 of the sheath layer 13. The sheath layer 13 thus enables total internal reflection at the boundary layer with respect to the core 11 and hence light guiding. At the same time, the sheath layer 13 can serve as a mechanical protective layer.

The optoelectrical guide/conductor arrangement 1 furthermore has a functional layer system 20, which can be embodied and producible in the same way as in FIG. 1.

As already explained, the functional layer system 20 can comprise a plurality of individual layers. The latter here are a base layer region 21 embodied as an adhesion promoter layer, the actual conductive layer 22 and an optional barrier layer (passivation layer) 23. With regard to the production of such an optoelectrical guide/conductor arrangement, the entire layer sequence can be implemented in succession in a batch cycle without interrupting the vacuum process, with the result that a plurality of components having optoelectrical guide/conductor arrangements 1 of this type can also be coated in parallel in a cost-effective manner.

Further exemplary embodiments of the production of an optoelectrical guide/conductor arrangement are described below.

Example 1: optoelectrical guide/conductor arrangement 1 having an optical waveguide 10 embodied as a quartz fiber with a core 11 having a diameter of 150 µm, a cladding 12 having a diameter of 180 µm, and a sheath layer 13 embodied as a polymer layer and composed of polyimide with an outer diameter of the optical waveguide 10 of overall approximately 210 µm.

A base layer region was produced by subjecting the sheath layer to a pretreatment. Ultrasonic cleaning using an alkaline or a neutral cleaning agent and IR drying was used in this case.

A conductive layer was applied consisting of a titanium coating having a thickness of 15 nm, which was produced by means of DC magnetron sputtering. The coating was effected in a vacuum at a process pressure of less than 1E-2 mbar. The sputtering target was chosen with a purity of 99%. The minimum distance between substrate and target was chosen to be 5 cm, the optical waveguide projecting into the plasma.

By means of a 4-point measuring instrument for determining the sheet resistance, a value of 10 ohms/sqr (wherein the unit ohm/sqr corresponds to the unit ohm) was measured. This corresponds to a resistivity of 1.5 E-5 ohm cm. The adhesion of the layer system was checked by means of an adhesion test according to DIN 58196-6 (1995 July). No detachments of the functional layer system from the optical waveguide were evident here.

Example 2: an optical waveguide embodied as a quartz fiber and having a sheath layer composed of polyimide was cleaned and preactivated by means of an atmospheric plasma in the form of a corona discharge. A coating was subsequently effected by means of reactive medium-frequency plasma of a silicon oxide coating, which was provided with a conductive molybdenum coating having a layer thickness of 24 nm without vacuum breach. This was followed by a passivation of this layer without vacuum breach by means of reactive magnetron sputtering with a silicon nitride coating having a layer thickness of 100 nm.

In a subsequent test of the sheet resistance, a sheet resistance of 5 ohms/sqr was determined by means of an inductive measurement method, an eddy current measuring instrument. No delaminations were able to be ascertained in accordance with the adhesion test mentioned above.

Example 3: an optical waveguide embodied as a quartz fiber and having a sheath layer composed of polyimide is cleaned by means of ultrasonic cleaning in accordance with example 1. The conductive layer applied directly to the sheath layer comprises molybdenum having a sheet resistance of 10 ohms/sqr. In order to protect the molybdenum coating, the coating of a barrier coating composed of TiO2 is optionally effected. Both coatings are produced in a magnetron sputtering process in a vacuum, wherein the optical waveguides project into the plasma and a virtually homogeneous coating is thus produced. The coatings are effected from a metallic sputtering target of purity 3N in the case of the molybdenum coating and, in the case of the TiO2 coating, from a metallic target or a partly ceramic target with the addition of oxygen. In this case, the $TiO_2$ coating is embodied as partly amorphous and partly anatase. In a subsequent mechanical loading test that involves pulling aluminum test bodies having a mass of 22.5 g over the length of the optical waveguides, no scratches or delaminations of the metallic coating are evident on the basis of micrographs recorded by a light microscope with up to 100× magnification.

Example 4: in a further exemplary embodiment, an optical waveguide embodied as a quartz fiber and having a sheath layer composed of polyimide is pretreated by means of wet-chemical cleaning. This is followed by applying layers both of the base layer region and of the conductive layer with the addition of oxygen and argon. In order to ensure an improved adhesion between sheath layer and conductive layer, an adhesion promoter layer composed of TiO2 is formed therebetween, wherein, for producing the latter, the ratio of oxygen to the total flow of oxygen and argon is less than 0.4. Afterward, as a conductive coating, a metallic titanium coating having a sheet resistance of 1 ohm/sqr is coated, wherein, for producing the latter, the ratio of oxygen to the total flow of oxygen and argon is less than 0.1. As additional passivation, a further TiO2 coating is applied, wherein, for producing the latter, the ratio of oxygen to the total flow of oxygen and argon is less than 0.7.

The ratio of oxygen to the total flow (see exemplary ratios mentioned above) indicates how close the result is to the metal character or the dielectric character of the TiO2 layer.

Figure 3:
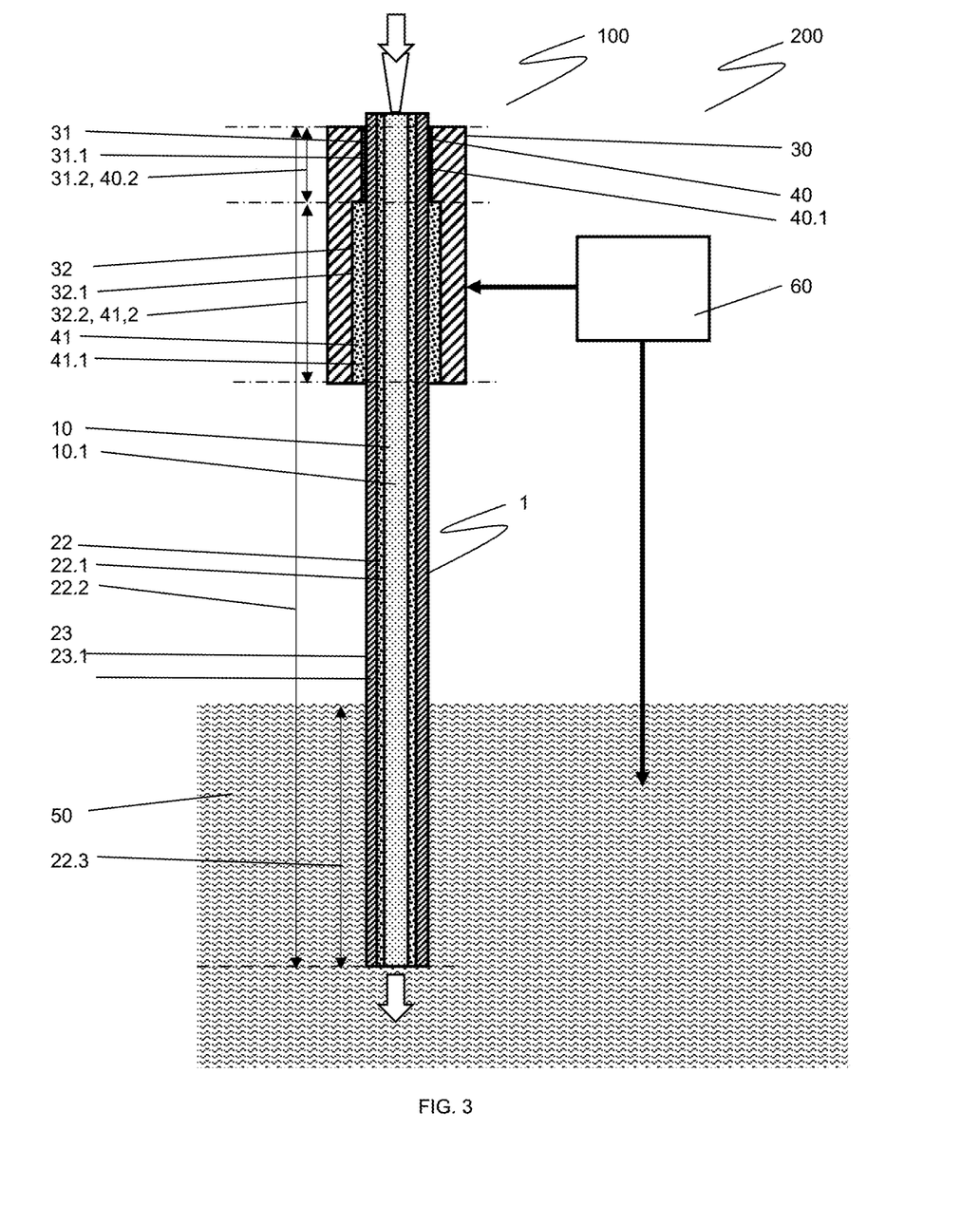
FIG. 3 shows a cross section through a device for detecting immersion (200) comprising an optoelectrical guide/conductor system (100) having an optoelectrical guide/conductor arrangement (1) and an adapter sleeve (30), which mechanically embraces the optoelectrical guide/conductor arrangement (1) and electrically contacts the conductive layer (22) thereof.

FIG. 3 shows a device 200 for detecting the immersion of an optoelectrical guide/conductor arrangement 1 of an optoelectrical guide/conductor system 100 in a conductive medium 50. Such a device 200 thus corresponds to a preferred application of such an optoelectrical guide/conductor arrangement 1 for filling level determination or for determining a penetration depth 22.3 into a conductive liquid 50. For this purpose, the optical waveguide 10 with its functional layer system 20 is secured in an electrically conductive adapter sleeve 30 and together with the latter forms an optoelectrical guide/conductor system 100. In the exemplary embodiment shown, the adapter sleeve is connected to an electrical evaluation unit 60, which can couple AC voltage signals for impedance measurement with a specific frequency f into the sleeve. Furthermore, the evaluation unit 60 is conductively connected to the liquid 50 via ground or directly, as shown in FIG. 3.

The electrically conductive adapter sleeve 30, which can consist of high-grade steel or nickel silver, for example, has a fixing section 31 with the diameter 31.1 thereof and the length 31.2 thereof for receiving the optoelectrical guide/conductor arrangement 1. Furthermore, the adapter sleeve 30 can have a separate contacting section 32 with the diameter 32.1 thereof and the length 32.2 thereof. The diameters 31.1 and 32.1 and also the lengths 31.2 and 32.2 can differ in this case. Preferably, the fixing section 31 has a small diameter 31.1, which is only slightly greater than the diameter of the complete optical waveguide 10 with the functional layer system 20 thereof, such that upon adhesive bonding with an adhesive 40, it is possible to achieve a position afforded the closest possible tolerance, and with a small centricity error, in order that an optimum coupling of light into the optically guiding core 11 of the optical waveguide 10 (cf. FIG. 1 or 2) can be achieved. In general, laser light focused onto the core 11 is coupled in here. Special adhesives 40 of very low viscosity are often used for this purpose, which adhesives, on account of the capillary effect, can fill the adhesive gap thus produced.

With regard to an electrical coupling, however, it may be necessary additionally to provide a conductive adhesive 41 in the contacting section 32. This type of adhesive generally involves silver-filled epoxy adhesives, although these require a larger adhesive gap. Therefore, the diameter 32.1 of the contacting section 32 of the adapter sleeve 30 is greater than the diameter 31.1 of the fixing section 31 of the adapter sleeve 30.

The optoelectrical guide/conductor system, i.e. the optoelectrical guide/conductor arrangement 1 with the adapter sleeve 30 and the adhesives 40, 41 used, then form an impedance which is dependent on the frequency f and which changes upon contact with the liquid 50 or upon immersion in the latter. Here in the contacting of the optoelectrical guide/conductor arrangement 1 in the adapter sleeve 30, care should be taken to ensure the lowest possible contact impedances, both capacitively and owing to ohmic conduction, in order to enable a sufficiently sensitive detection of the filling level of the liquid or the immersion depth 22.3.

If this arrangement is considered at typical frequencies in the range of a few hundred hertz to approximately 100 kHz, inductive impedances can be disregarded, thus resulting in an electrical equivalent circuit diagram composed substantially of ohmic resistances and capacitors yielding the frequency-dependent total impedance Z.

Figure 4A:
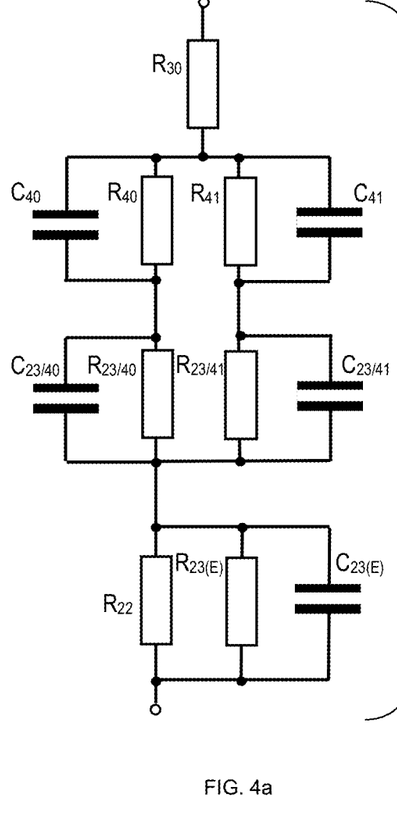
FIG. 4a shows an equivalent circuit diagram for the total impedance of an optoelectrical guide/conductor system (100)

Thus, to an approximation it is possible to outline schematically an equivalent circuit diagram as illustrated in FIG. 4a. Here, $R_{30}$ is the ohmic resistance of the sleeve 30 (comparatively low resistance, in the mΩ range).

$R_{40}$ is the ohmic resistance of the adhesive gap for the adhesive 40 between optical waveguide 10 and functional layer system 20, depending on the adhesive layer thickness 40.1 $d_{K40Q}$ and the adhesive gap length 40.2 $l_{K40Q}$ and also the resistivity $\varrho_{K40}$ of the adhesive 40 (the latter has a comparatively high value).

$C_{40}$ is the capacitance of the adhesive gap with the adhesive 40, depending on the adhesive layer thickness 40.1 $d_{K40Q}$, the adhesive gap length 40.2 $l_{K40Q}$ and the total diameter $d_{Fg}$ of the optical waveguide 10 including the functional layer system 20 $d_{Fg}$ and also the relative permittivity $\varepsilon_{K40}$ of the adhesive 40.

$R_{41}$ is the ohmic resistance of the adhesive gap for the conductive adhesive 41 between optical waveguide 10 and functional layer system 20, depending on the adhesive layer thickness 41.1 $d_{K41Q}$ and the adhesive gap length 41.2 $l_{K41Q}$ and also the resistivity $\varrho_{K41}$ of the conductive adhesive 41 (the latter has a comparatively low value).

$C_{41}$ is the capacitance of the adhesive gap with the conductive adhesive 41, depending on the conductive adhesive layer thickness 41.1 $d_{K41Q}$ and the adhesive gap length 40.2 $l_{K41Q}$ and also the relative permittivity $\varepsilon_{K41}$ of the conductive adhesive 41.

$R_{23/40}$ is the ohmic resistance of the barrier layer 23 of the functional layer system 20 in the region of the adhesive bonding with the adhesive 40, depending on its barrier layer thickness 23.1 $d_{23}$ and the adhesive gap length 40.2 $l_{K40Q}$ and also the resistivity of the barrier layer 23 $\varrho_{23}$ (generally very high value).

$C_{23/40}$ is the capacitance of the barrier layer 23 of the functional layer system 20 in the region of the adhesive bonding with the adhesive 40, depending on its barrier layer thickness 23.1 $d_{23}$ and the adhesive gap length 40.2 $l_{K40Q}$ and also the relative permittivity $\varepsilon_{23}$ of the barrier layer 23.

$R_{23/41}$ is the ohmic resistance of the barrier layer 23 of the functional layer system 20 in the region of the adhesive bonding with the conductive adhesive 41, depending on its barrier layer thickness 23.1 $d_{23}$ and the adhesive gap length 41.2 $l_{K41Q}$ and also the resistivity of the barrier layer 23 $\varrho_{23}$ (generally very high value).

$C_{23/41}$ is the capacitance of the barrier layer 23 of the functional layer system 20 in the region of the adhesive bonding with the conductive adhesive 41, depending on its barrier layer thickness 23.1 $d_{23}$ and the adhesive gap length 41.2 $l_{K40Q}$ and also the relative permittivity $\varepsilon_{23}$ of the barrier layer 23.

$R_{22}$ is the ohmic resistance of the conductive layer 22, depending on the conductive layer thickness $d_{22}$ and conductive layer length 22.2 $l_{22}$ and also the resistivity of the conductive layer 22 $\varrho_{22}$, which has a comparatively low value.

$R_{23(E)}$ is the ohmic resistance of the barrier layer 23 depending on immersion depth 22.3 E and the barrier layer thickness 23.1 $d_{23}$ and the resistivity of the barrier layer 23 $\varrho_{23}$.

$C_{23(E)}$ is the capacitance of the barrier layer 23 of the functional layer system 20 in the region of immersion, depending on its barrier layer thickness 23.1 $d_{23}$ and the immersion depth 22.3 E and also the relative permittivity $\varepsilon_{23}$ of the barrier layer 23.

This equivalent circuit diagram in FIG. 4a can be simplified insofar as the ohmic resistance $R_{30}$ of the adapter sleeve 30 is virtually negligible since it is in the mΩ range. Furthermore, the ohmic resistance of the adhesive gap $R_{40}$ for the adhesive 40 has a comparatively high value and thus contributes only very little to the total impedance. This also applies to the ohmic resistance $R_{23/40}$ of the barrier layer 23 in the region of the adhesive 40. The same also applies to the ohmic resistance $R_{23/41}$ of the barrier layer 23 in the region of the conductive adhesive 41. On the other hand, it is possible to disregard the capacitive portion of the adhesive gap $C_{41}$ with the conductive adhesive 41 in relation to $R_{41}$. It is likewise possible to disregard the ohmic resistance $R_{23(E)}$ of the barrier layer 23 depending on the immersion depth 22.3 E since this portion contributes very little to the conductivity on account of the high resistance of the barrier layer 23. This yields the simplified equivalent circuit diagram in FIG. 4b for the total impedance Z.

Figure 4B:
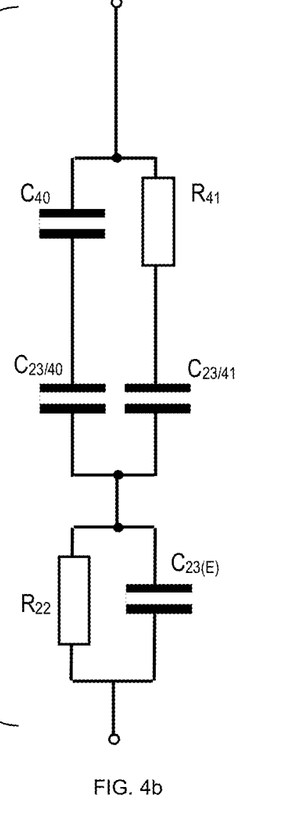
FIG. 4b: shows a simplified equivalent circuit diagram for the total impedance of an optoelectrical guide/conductor system (100).

The individual impedances from the simplified equivalent circuit diagram in FIG. 4b are calculated here as follows:

$$C_{40} \varepsilon_0 \varepsilon_{K40} \pi d_{Fg} l_{K40Q}/d_{K40Q} \quad (1)$$

$$C_{23/40} = \varepsilon_0 \varepsilon_{23} \pi (d_F + 2d_L) l_{K40Q}/d_{23} \quad (2)$$

where $d_F$ is equal to the diameter 10.1 of the optical waveguide 10 including the conductive layer thickness 22.1 $d_L$ of the functional layer system 20 and the barrier layer thickness 23.1 $d_{23}$ $$R_{41} = \varrho_{K41} d_{K41Q}/(\pi l_{K41Q} d_{Fg}) \quad (3)$$

$$C_{23/41} = \varepsilon_0 \varepsilon_{23} \pi (d_F + 2d_L) l_{K41Q}/d_{23} \quad (4)$$

$$R_{22} = \varrho_{22} 4 l_F / (((d_F + 2d_{22})^2 - d_F^2)\pi) \quad (5)$$

$$C_{23(E)} = \varepsilon_0 \varepsilon_{23} \pi d_{Fg} E / d_{23} \quad (6)$$

In accordance with one exemplary embodiment, for a functional layer system 20 having a conductive layer 22 composed of titanium (Ti) and a barrier layer 23 composed of $TiO_2$, the following individual impedances result taking into account the following geometries, material constants and frequencies f:

first frequency $f_1$: 1.000 1/s
second frequency $f_2$: 10.000 1/s
diameter 10.1 of optical waveguide 10: 265 µm=2.65 E-4 m
conductive layer thickness 22.1 of the Ti conductive layer: 0.4 µm=0.4 E-6 m
barrier layer thickness 23.1 of $TiO_2$: 100 nm=0.1 E-6 m
adhesive layer thickness 40.1 of the adhesive 40: 20 µm=2 E-5 m
adhesive gap length 40.2 for the adhesive 40: 0.8 mm=8 E-4 m
adhesive layer thickness 41.1 of the conductive adhesive 41: 0.1 mm=1 E-4 m
adhesive gap length 41.2 for the conductive adhesive 41: 1.5 mm=1.5 E-3 m
conductive layer length 22.2: 50 mm=5 E-2 m
$\varepsilon_0$: 8.85 E-12 As/Vm
$\varepsilon_{23}$: 180
$\varepsilon_{40}$: 10
$\varrho_{22}$: 4.0 E-7 ohm m
$\varrho_{41}$: 1.0 E-6 ohm m
first immersion depth 22.3 E: 0 mm
(fiber end just touches the liquid 50)
second immersion depth 22.3 E: 10 mm=1 E-2 m
third immersion depth 22.3 E: 20 mm=2 E-2 m
$C_{40}$=3.0 pF
$C_{23/40}$=11 nF
$R_{41}$=0.08 mΩ
$C_{23/41}$=20 nF
$R_{22}$=60Ω
$C_{23(E=0)}$=0 F
Given an immersion depth E=10 mm=1 E-2 m:
$C_{23(E=10)}$=0.13 µF
Given an immersion depth E=20 mm=2 E-2 m:
$C_{23(E=20)}$=0.27 µF The following frequency-dependent absolute individual impedances thus result, with $XC_i$ representing capacitive reactive-power reactances and $ZR_i$ representing real ohmic resistances, where $$XC_i = 1/\omega C_i = 1/(2\pi f\, C_i) \quad (7)$$

$$ZR_i = R_i \quad (8)$$

The following values result for the first frequency $f_1$=1 kHz:

$XC_{40}$=54 MΩ
$XC_{23/40}$=15 kΩ
$ZR_{41}$=0.08 mΩ
$XC_{23/41}$=8 kΩ
$ZR_{22}$=60Ω
$XC_{23(E=0\ mm)}$ extremely high value
$XC_{23(E=10\ mm)}$ 1.2 kΩ
$XC_{23(E=20\ mm)}$ 600Ω

The following values result for the second frequency $f_2$=10 kHz:

$XC_{40}$=5.4 MΩ
$XC_{23/40}$=1.5 kΩ
$ZR_{41}$=0.08 mΩ
$XC_{23/41}$=800Ω
$ZR_{22}$=60Ω
$XC_{23(E=0\ mm)}$ extremely high value
$XC_{23(E=10\ mm)}$ 120Ω
$XC_{23(E=20\ mm)}$ 60Ω

The exemplary values show that with an appropriate choice of frequency and use of a conductive adhesive 41 in the contacting section 32, very good impedance relations occur, such that a filling level detection or measurement of the penetration depth 22.3 E is possible with comparatively simple electronic outlay within the evaluation unit 60.

In the case where the optoelectrical guide/conductor system 100 does not comprise a barrier layer 23, acting in particular as an insulator, in particular only contact resistances are still of significance. In such a case, for example, but in principle also independently thereof, DC voltage signal input couplings can also be used.

It is evident to the person skilled in the art that the embodiments described above should be understood to be by way of example and the invention is not restricted thereto, but rather can be varied in diverse ways, without departing from the scope of protection of the claims. Moreover, the features of the optoelectrical guide/conductor arrangement are also disclosed, mutatis mutandis, as features for the method for producing an optoelectrical guide/conductor arrangement, and vice versa. Features, irrespective of whether they are disclosed in the description, the claims, the figures or elsewhere, also individually define constituent parts of the invention, even if they are described jointly together with other features.

LIST OF REFERENCE SIGNS

100 Optoelectrical guide/conductor system
1 Optoelectrical guide/conductor arrangement
10 Optical waveguide
10.1 Diameter
11 Optically guiding core
12 Cladding
13 Organic sheath layer
20 Functional layer system
20.1 Layer thickness
21 Base layer region
22 Conductive layer
22.1 Conductive layer thickness
22.2 Conductive layer length
22.3 Immersion depth
23 Barrier layer
23.1 Barrier layer thickness
30 Adapter sleeve
31 Fixing section
31.1 Diameter
31.2 Length
32 Contacting section
32.1 Diameter
32.2 Length
40 Adhesive
40.1 Adhesive layer thickness
40.2 Adhesive gap length
41 Conductive adhesive
41.1 Conductive adhesive layer thickness
41.2 Adhesive gap length
50 Liquid
60 Evaluation unit
200 Device for detecting immersion

What is claimed is:

1. An optoelectrical guide/conductor system, comprising:
   an optoelectrical guide/conductor arrangement comprising an optical waveguide and a conductive layer, the optical waveguide having an outer, organic sheath layer, wherein the conductive layer is a single layer or a sequence of layers and is directly or indirectly on the outer sheath layer;
   an adapter sleeve in which the optoelectrical guide/conductor arrangement is inserted in such a way that the optoelectrical guide/conductor arrangement projects from the adapter sleeve,
   wherein the adapter sleeve has an outer sleeve body enclosing an inner receiving opening along a sleeve axis, and wherein the optoelectrical guide/conductor arrangement extends along the sleeve axis through the inner receiving opening;
   wherein the adapter sleeve has a conductive contacting section, the adapter sleeve mechanically embraces the optoelectrical guide/conductor arrangement with the conductive contacting section in electrical contact with the conductive layer so as to transmit electrical signals between the conductive layer and the conductive contacting section; and
   an electrically conductive adhesive fixing the adapter sleeve and the optoelectrical guide/conductor arrangement to one another, wherein the electrically conductive adhesive is between and electrically connecting the conductive layer and the conductive contacting section; and
   wherein the adapter sleeve further comprises a fixing section adjacent to the conductive contacting section, that mechanically embraces the optoelectrical guide/conductor arrangement; and
   a fixing adhesive at the fixing section, wherein the fixing adhesive has a lower viscosity than the electrically conductive adhesive.

2. The system of claim 1, wherein the inner receiving opening is cylindrical and/or is arranged concentrically with respect to the outer sleeve body.

3. The system of claim 1, wherein the optoelectrical guide/conductor embraced in the adapter sleeve in such a way that at least the optical waveguide is accessible from both sides of the adapter sleeve.

4. The system of claim 1, wherein the fixing section mechanically embraces the optoelectrical guide/conductor arrangement with a radial tolerance of less than 50 μm and/or with a concentricity error of less than 50 μm.

5. The system of claim 1, wherein the adapter sleeve is made of a material selected from a group consisting of metal, high-grade steel, nickel silver, conductive plastic, and conductive ceramic.

6. The system of claim 1, wherein the adapter sleeve has an ohmic resistance ($R_{30}$) between 1 and 1000 milliohms, and/or wherein the conductive layer has an ohmic resistance ($R_{22}$) between 1 and 1000 ohms.

7. The system of claim 1, wherein the conductive layer further comprises a barrier layer configured to inhibit diffusion of oxygen and/or ions of acidic or alkaline solutions into the conductive layer, and
   wherein the barrier layer has a hardness of at least 800 HV in accordance with the test standard DIN EN ISO 14577-4:2007-8.

8. The system of claim 1, wherein the conductive layer further comprises a barrier layer configured to inhibit diffusion of oxygen and/or ions of acidic or alkaline solutions into the conductive layer, and
   wherein the barrier layer comprises a material selected from a group consisting of nitride, carbide, boride, oxynitride, carbonitride, $Si_3N_4$, BN, AlN, TiN, AlSiN, SiON, SiAlON, oxide of Si, oxide of Al, oxide of Ti, oxide of Zr, oxide of Zn, oxide of Sn, oxide of Ta, oxide of Nb, oxide of Y, $TiO_2$, $SiO_2$, and alloys or ternary systems thereof.

9. The system of claim 1, further comprising a measurable impedance (Z) between the adapter sleeve and the optoelectrical guide/conductor arrangement, wherein the measurable impedance (Z) has a first portion from the conductive layer and a second portion from the conductive adhesive, wherein the second portion is less than or equal to 10 times the first portion.

10. The system of claim 9, wherein the second portion is less than or equal to 0.5 times the first portion.

11. The system of claim 9, wherein the first portion is dependent on a parameter selected from a group consisting of: an impedance of the conductive layer, an impedance of the conductive layer with respect to a medium surrounding the optoelectrical guide/conductor arrangement, and combinations thereof, and/or
   wherein the second portion is dependent on a parameter selected from a group consisting of: an ohmic resistance ($R_{40}$) of the conductive adhesive, a capacitive reactance ($C_{40}$) of the conductive adhesive, an ohmic resistance ($R_{23/40}$) of a barrier layer configured to inhibit diffusion of oxygen and/or ions of acidic or alkaline solutions into the conductive layer, a capacitive reactance ($C_{23/40}$) of the barrier layer, and any combinations thereof.

12. The system of claim 9, wherein the measurable impedance is measurable between an outer sleeve body of the adapter sleeve and an end region of the conductive layer projecting from the adapter sleeve.

13. The system of claim 1, wherein the optical waveguide comprises a core with a cladding that surrounds the core, the cladding is between the core and the outer sheath layer, and wherein the core has a refractive index that is greater than a refractive index of the outer sheath layer and/or is greater than a refractive index of the cladding.

14. The system of claim 1, wherein the outer sheath layer comprises a material selected from a group consisting of polyamide (PA), polyimide (PI), polymethyl methacrylate (PMMA), wax, waxlike constituents, and alkylsilane.

15. The system of claim 1, further comprising a functional layer system on the outer sheath layer, the functional layer system having a base layer region, wherein the conductive layer is on the base layer region.

16. The system of claim 13, wherein the base layer region comprises a material selected from a group consisting of an oxide, $SiO_2$, $TiO_2$, $Al_2O_3$, $SnO_2$, $HfO_2$, a boride, carbide, nitride, oxynitride, carbonitride, a metal, Si, Ti, Mo, and Cr.

17. The system of claim 1, wherein the conductive layer comprises a material selected from a group consisting of titanium, silicon, aluminum, gold, silver, molybdenum, tungsten or zirconium, and alloys thereof.

18. A device for detecting the immersion of an optoelectrical guide/conductor arrangement in a conductive medium, comprising:
   the optoelectrical guide/conductor system of claim 1;
   an evaluation unit electrically connected to the adapter sleeve and the conductive medium, wherein the evaluation unit is configured to determine an impedance or change in impedance between the adapter sleeve and the medium so that immersion of the optoelectrical guide/conductor arrangement in the medium is detected and/or an immersion depth of the optoelectrical guide/conductor arrangement in the medium is determined.

19. The system of claim 4, wherein the fixing adhesive has a viscosity configured to maintain the radial tolerance and/or the concentricity error.

20. An optoelectrical guide/conductor system, comprising:
- an optoelectrical guide/conductor arrangement comprising an optical waveguide and a conductive layer, the optical waveguide having an outer, organic sheath layer, the conductive layer is a single layer or a sequence of layers, the conductive layer is directly or indirectly on the outer sheath layer;
- an adapter sleeve in which the optoelectrical guide/conductor arrangement is inserted in such a way that the optoelectrical guide/conductor arrangement projects from the adapter sleeve,
- wherein the adapter sleeve has an outer sleeve body enclosing an inner receiving opening along a sleeve axis, and wherein the optoelectrical guide/conductor arrangement extends along the sleeve axis through the inner receiving opening;
- wherein the adapter sleeve has a conductive contacting section, the adapter sleeve mechanically embraces the optoelectrical guide/conductor arrangement with the conductive contacting section in electrical contact with the conductive layer so as to transmit electrical signals between the conductive layer and the conductive contacting section;
- an electrically conductive adhesive fixing the adapter sleeve and the optoelectrical guide/conductor arrangement to one another,
- wherein the conductive layer further comprises a barrier layer configured to inhibit diffusion of oxygen and/or ions of acidic or alkaline solutions into the conductive layer, and
- wherein the electrically conductive adhesive contacts the conductive layer directly or indirectly; and
- wherein the adapter sleeve further comprises a fixing section adjacent to the conductive contacting section, that mechanically embraces the optoelectrical guide/conductor arrangement; and
- a fixing adhesive at the fixing section, wherein the fixing adhesive has a lower viscosity than the electrically conductive adhesive.

21. A method for producing an optoelectrical guide/conductor system, comprising:
- providing an adapter sleeve having a conductive contacting section, wherein the adapter sleeve has a fixing section adjacent to the conductive contacting section, and an outer sleeve body enclosing an inner receiving opening along a sleeve axis;
- providing an optical waveguide having an outer, organic sheath layer and a conductive layer with of a single layer or a sequence of layers, the conductive layer being applied directly or indirectly on the outer sheath layer;
- applying an electrically conductive adhesive to a portion of the conductive contacting section, and further applying a fixing adhesive to a portion of the fixing section, wherein the fixing adhesive has a lower viscosity than the electrically conductive adhesive; and
- inserting the optical waveguide into the adapter sleeve in such a way that the optical waveguide projects from the adapter sleeve and that the optical waveguide extends along the sleeve axis through the inner receiving opening and that the fixing section of the adapter sleeve mechanically embraces the optical waveguide and that the conductive contacting section and the conductive layer are in electrical contact with one another through the electrically conductive adhesive so as to transmit electrical signals between the conductive layer and the conductive contacting section and that the fixing adhesive at the fixing section fixes the optical waveguide to the adapter sleeve.

* * * * *